United States Patent
Bermudez Agudelo et al.

(10) Patent No.: US 10,251,829 B2
(45) Date of Patent: Apr. 9, 2019

(54) COMBINED CARE AND STYLING AGENT HAVING A HEATING ELEMENT EFFECT

(71) Applicant: Henkel AG & Co. KGaA, Duesseldorf (DE)

(72) Inventors: Maria Catalina Bermudez Agudelo, Darmstadt (DE); Anna Puls, Winsen (DE); Julia Bibiane Lange, Bad Bramstedt (DE); Cyrielle Martinez, Hamburg (DE); Bernd Richters, Hamburg (DE)

(73) Assignee: Henkel AG & Co. KGaA (DE)

( * ) Notice: Subject to any disclaimer, the term of this patent is extended or adjusted under 35 U.S.C. 154(b) by 1 day.

(21) Appl. No.: 15/619,403

(22) Filed: Jun. 9, 2017

(65) Prior Publication Data
US 2017/0273891 A1   Sep. 28, 2017

Related U.S. Application Data

(63) Continuation of application No. PCT/EP2015/074945, filed on Oct. 28, 2015.

(30) Foreign Application Priority Data

Dec. 11, 2014 (DE) .................. 10 2014 225 546

(51) Int. Cl.
| | |
|---|---|
| *A61K 8/86* | (2006.01) |
| *A61K 8/37* | (2006.01) |
| *A61Q 5/06* | (2006.01) |
| *A61K 8/25* | (2006.01) |
| *A61K 8/81* | (2006.01) |
| *A61K 8/85* | (2006.01) |
| *A61K 8/34* | (2006.01) |

(52) U.S. Cl.
CPC .............. *A61K 8/86* (2013.01); *A61K 8/25* (2013.01); *A61K 8/345* (2013.01); *A61K 8/37* (2013.01); *A61K 8/8176* (2013.01); *A61K 8/8182* (2013.01); *A61K 8/85* (2013.01); *A61Q 5/06* (2013.01); *A61K 2800/242* (2013.01); *A61K 2800/31* (2013.01); *A61K 2800/594* (2013.01)

(58) Field of Classification Search
CPC ... A61Q 5/06; A61K 8/37; A61K 8/86; A61K 8/85; A61K 8/25; A61K 8/345; A61K 8/8182; A61K 8/8186; A61K 2800/242; A61K 2800/31; A61K 2800/594
See application file for complete search history.

(56) References Cited

U.S. PATENT DOCUMENTS

| | | |
|---|---|---|
| 4,938,954 A | 7/1990 | Gross et al. |
| 5,538,720 A | 7/1996 | Jendryssek-Pfaff et al. |

FOREIGN PATENT DOCUMENTS

| | | |
|---|---|---|
| EP | 0027730 A2 | 4/1981 |
| EP | 1226812 A2 | 12/2001 |
| JP | 2006124352 A | 5/2006 |
| JP | 2007126371 A | 5/2007 |
| WO | WO 01/72262 A2 * | 10/2001 |
| WO | 03037281 A1 | 5/2003 |
| WO | 2009015108 A1 | 1/2009 |
| WO | 2012012084 A2 | 1/2012 |

OTHER PUBLICATIONS

Masuda et al. (JP 2006 124352, Eng. Translation, 2006.*
Argembeaux et al. (EP 1 226 812 A2, English translation, Description, Jul. 2002.*
Argembeaux et al. (EP 1 226 812 A2, English translation, Claims, Jul. 2002.*
PCT International Search Report (PCT/EP2015/074945) dated Jun. 20, 2016.
Alexander P: "Dressing Up Hair", Manufacturing Chemist, H P C I Media Ltd, UK, vol. 62, No. 2, Feb. 1991 (Feb. 1991), XP000202282, ISSN: 0262-4230 the whole document.
Anonymous: "Moisturizing Hair Styling Powder", Feb. 2013 (Feb. 2013), pp. 1-2, XP055194861, Retrieved from the Internet: URL:https://www.aerosil.com/sites/lists/IM/Documents/GF-Moisturizing-Hair-Styling-Powder-EN.pdf [retrieved on Jun. 10, 2015] the whole document.
Hasenzahl S et al: "Fumed silica for personal care and cosmetics—versatile and effective", SOFW-Journal Seifen, Oele, Fette, Wachse, Verlag Fur Chemische Industrie, Augsburg, DE, Aug. 2003 (Aug. 2003), pp. 1-8, XP002289365, ISSN: 0942-7694 p. 5.
"Chemsil: Low Viscosity Liquid Lubricant", Cosmetics & Toiletries, Wheaton, IL, US, vol. 124, No. 5, May 2009 (May 2009), p. 96, XP009190180, ISSN: 0361-4387 the whole document.
"Graham Webb by Graham Webb: Brit Style Exothermic Medium Hold Gel 8.5 OZf", 2012, XP002758278, Retrieved from the Internet: URL:http://www.amazon.com/Graham-Webb-Graham-Webb-EXOTHERMIC/dp/B001B7G2T4 [retrieved on May 31, 2016] the whole document.
Steffen Wolf: "Haarstyling", haut.de, Sep. 24, 2015 (Sep. 24, 2015), pp. 1-23, XP055277281, Retrieved from the Internet: URL:http://www.haut.de/wp-content/uploads/aut-de haar haarstyling.pdf [retrieved on Jun. 2, 2016] the whole Document.

* cited by examiner

*Primary Examiner* — Blessing M Fubara
(74) *Attorney, Agent, or Firm* — P. Scott Smith

(57) ABSTRACT

Cosmetic composition having a heating effect and used for the care and temporary shaping of keratin fibers and related methods are provided. The cosmetic composition can include at least one polyethylene glycol comprising 4 to 20 oxyethylene units; a copolymer composed of hydrogenated castor oil and an n-alkyl dicarboxylic acid comprising 4 to 10 C atoms; and at least one film-forming agent.

10 Claims, No Drawings

COMBINED CARE AND STYLING AGENT HAVING A HEATING ELEMENT EFFECT

FIELD OF THE INVENTION

The present invention generally relates to a cosmetic composition as a hair fixative or for temporarily shaping keratin fibers, in particular human hair, and for keratin fiber care, said composition having a heating effect. The cosmetic composition of the invention includes at least one polyethylene glycol comprising 4 to 20 oxyethylene units, a copolymer composed of hydrogenated castor oil and an n-alkyl dicarboxylic acid comprising 4 to 10 C atoms, and (c) at least one film-forming agent.

BACKGROUND OF THE INVENTION

The temporary shaping of hairstyles lasting for an extended period of up to several days normally requires the use of active ingredients having a fixative effect. As a result, an important role exists for hair treatment agents serving to temporarily shape the hair. Corresponding means used for temporary shaping normally include synthetic polymers and/or waxes as active ingredients having a fixative effect. Temporary hair shaping agents may be manufactured as, for example, hair spray, hair wax, hair gel or hair mousse.

The most important property of a means used for temporarily shaping hair, hereinafter referred to as a styling agent, consists of holding the treated fibers in their newly configured form—meaning the form imparted to the hair—in the strongest possible manner. Mention is also commonly made of a styling hold or the styling agent having a good ability to hold a hair set. The styling hold is essentially determined by the type and quantity used of the active ingredients having a fixative effect, but the additional components of the styling agent can also be influential.

In addition to a high degree of hold, styling agents can fulfill a number of additional requirements. These can be roughly divided into the properties of the hair, the properties of the respective formulation such as the foam, the gel or the aerosol spray properties, and properties concerning the handling of the styling agent, whereby the properties of the hair are particularly important. Particularly noteworthy are moisture resistance, lack of stickiness (tackiness) and a balanced conditioning effect. Furthermore, a styling agent should be usable for the widest possible variety of hair types and be mild on the hair and skin.

In order to meet the various requirements, a large number of synthetic polymers have already been developed as active ingredients having a fixative effect for use in styling agents. The polymers can be divided into cationic, anionic, nonionic and amphoteric polymers having a fixative effect. Waxes are used as alternative or additional active ingredients having a fixative effect.

The application of the polymers and/or waxes ideally results in a polymer film, more specifically a film providing the hairstyle with a strong hold, which is sufficiently flexible while at the same time not breaking under stress. If the (polymer) film is too brittle, it can allow for the formation of film residues which detach with movement of the hair, giving the impression that the person using the respective styling agent has dandruff.

In addition to temporarily shaping the hair, so-called styling, there also often is a need to care for the hair, which is frequently stressed or damaged due to external conditions such as sunlight, or hair treatments such as dyeing or bleaching. Hair care means normally include hair rinses (conditioners) and hair treatments as well as shampoos having a hair care effect. The active ingredient having a hair care effect included in these products is a lipophilic raw material, for example oils, fats or waxes. Hair care means have the aim of restoring the cuticle layer of the hair (cuticula), which can become damaged due to external factors. One known ingredient in hair care means such as shampoos and conditioners which is able to repair the cuticle layer is commercially available under the name Crodabond® CSA (company name Croda). It is a copolymer composed of hydrogenated castor oil and sebacic acid. The use of this copolymer in mascaras is described in WO 2012012084 A2.

The impression of a hair care effect can be enhanced for the user if, when applied to the hair, the cosmetic composition generates heat, or rather a heating effect will simply be experienced as being pleasant. Substances used in the cosmetics industry and able to achieve a heating effect are, for example, polyethylene glycol. Up to a certain length, these are hygroscopic and generate heat when coming into contact with water or moisture. Heat-generating compositions including polyethylene mixtures are commercially available under the name XO Therm® (Chemsil Silicones Inc.). These are mixtures of PEG-4, PEG-8 and PVP as well as, where applicable, polypolypropylene glycol. The manufacturer specifies that they are suitable for skin care, body care and feminine hygiene.

BRIEF SUMMARY OF THE INVENTION

It is an object of the present invention to provide cosmetic compositions suitable for both the care and the temporary shaping of keratin fibers and that demonstrate a heating effect during their application. In doing so, properties required specifically for styling agents such as good film-forming and/or fixative properties, a high degree of hold, flexibility, as few visible residues as possible and easy application to and distribution in the hair should be achieved or maintained.

A cosmetic composition having a heating effect and used for the care and temporary shaping of keratin fibers including:
  a. at least one polyethylene glycol comprising 4 to 20 oxyethylene units,
  b. a copolymer composed of hydrogenated castor oil and an n-alkyl dicarboxylic acid comprising 4 to 10 C atoms and
  c. at least one film-forming agent.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

According to the invention, this will be attained through combining certain hair care components and heat-generating components with one or more film-forming agents.

In the context of the present invention, it was unexpectedly determined that a styling agent could be provided which, through the combination of certain components, would also work as a hair care product, the application of which would achieve a heating effect. Through the use of the components described below, the hair care effect, the styling effect and the heating effect can be enhanced and/or modified.

In terms of the invention, the term keratin fibers comprises furs, wools and feathers, but human hair in particular.

The means according to the invention shall include as component (a) at least one polyethylene glycol comprising 4 to 20 oxyethylene units. As indicated earlier, polyethylene glycols are hygroscopic up to a certain chain length, whereby their hygroscopic behavior diminishes as the chain length increases, and they generate heat when coming into contact with water or moisture. The heating effect is achieved through component (a) when the cosmetic means according to the invention comes into contact with wet hair. The polyethylene glycol preferably comprises 4 to 10 oxyethylene units, more preferably 4 to 8 oxyethylene units. The polyethylene glycol (a) may preferably be a mixture of two or more polyethylene glycols. Particularly preferable in terms of the invention is a mixture of PEG-4 and PEG-8. Particularly preferable in terms of the invention is the use of mixtures including PEG-4 and PEG-8 which are commercially available under the name XO-Therm® (Chemsil Silicones Inc.). Preferred examples are specified as XO Therm® SP (INCI: PEG-4 (and) PEG-8 (and) PVP; viscosity RVT #2 @ 20 rpm: 1900 cs), XO Therm® CG (INCI: PEG-4 (and) PEG-8 (and) PVP; viscosity RVT #2 @ 20 rpm: 550 cs), XO Therm® IG (INCI: PEG-4 (and) PEG-8 (and) PVP; viscosity RVT #2 @ 20 rpm: 550 cs) nd XO Therm® LH (INCI: propylene glycol (and) PEG-4 (and) PEG-8 (and) PVP; viscosity RVT #2 @ 20 rpm: 150 cs).

The polyethylene glycol or the polyethylene glycols comprising 4 to 20 oxyethylene units according to the invention are included in a quantity such that a warming effect will be perceived when coming in contact with wet skin, for example when rubbed between wet hands. According to the invention, component (a) is preferably included in a quantity of approximately 15 to 75% by weight based on the total weight of the cosmetic composition, preferably approximately 20 to 70% by weight, and further preferably approximately 45 to 65% by weight.

If a mixture of two polyethylene glycols is used as component (a), for example the preferred combination of PEG-4 and PEG-8, the weight ratio between the two PEGs is preferably 90/10 to 10/90, preferably 70/30 to 30/70 and further preferably 60/40 to 40/60, or about 50/50.

In order for the heating effect to be achieved when coming in contact with wet hair or also with wet hands, the cosmetic composition of the present invention is generally free of water, meaning that it includes essentially no free water, preferably less than 1.0% by weight free water, further preferably less than 0.5% by weight free water based on the total weight of the cosmetic composition.

The cosmetic composition according to the invention furthermore includes as hair care component (b) a copolymer composed of hydrogenated castor oil and an n-alkyl dicarboxylic acid comprising 4 to 10 C atoms, preferably an oligoester of hydrogenated castor oil and sebacic acid. These compounds and the reparative effect they have on damaged hair in combination with an oil component are described, for example, in JP 2006124352 A. Preferable in terms of the invention is an oligoester of hydrogenated castor oil and sebacic acid (C10). Hydrogenated castor oil includes as a main component hydrogenated triricinolein (a triglyceride of hydrogenated ricinoleic acid). The OH groups at position 12 of two of the hydrogenated ricinol acid residues in the triricinolein are esterified with a carboxyl group from the dicarboxylic acid. According to the invention, this is preferably an oligomer with 3 to 12 repeating units, further preferably 4 to 10 repeating units. Particularly preferable as component (b) is commercially available as Crodabond® CSA and has the INCI name Hydrogenated Castor Oil/Sebacic Acid Copolymer (company name Croda), which exists as a pale yellow viscous liquid at ambient temperature.

The copolymer (b) composed of hydrogenated castor oil and an n-alkyl dicarboxylic acid comprising 4 to 10 carbon atoms is included in the cosmetic composition according to the invention in the quantity of 0.1 to 2% by weight, preferably 0.5 to 1.5% by weight based on the total weight of the cosmetic composition.

In preferred embodiments, the cosmetic composition in the present invention includes glycerin as an additional hair care substance, preferably at a purity of 99.0% by weight or higher, further preferably 99.5% by weight or higher. The glycerol simultaneously serves as a cosmetically acceptable carrier. Other cosmetically acceptable carriers, such as ethylene glycol, 1,2-propanediol or low alcohols comprising 1 to 4 carbon atoms such as isopropanol may also be included. The cosmetic composition according to the invention includes a quantity of glycerine preferably 10% by weight or more, preferably up to 20 to 80% by weight, further preferably 20 to 40% by weight and most preferably 25 to 35% by weight.

The cosmetic composition according to the invention furthermore includes at least one film-forming agent (c) to fulfill the styling agent function. The film-forming agent is preferably at least polyvinylpyrrolidone. Alternatively or additionally, a cationic and/or amphiphilic polymer may be included, in particular a quaternary ammonium compound. It is preferable, however, that polyvinylpyrrolidone (PVP) is included as a film-forming agent. It is further preferred that a combination of polyvinylpyrrolidone and a quaternary ammonium compound is included, in particular polyquaternium-46.

Polyvinylpyrrolidone is a vinylpyrrolidone homopolymer. It is preferable in terms of the invention to select the vinylpyrrolidone homopolymer from vinylpyrrolidone homopolymers having a K value (1% by weight solution of PVP, Brookfield at 23 [deg.] C.) of from 20 to 100 in water. Further preferable is a K value from 80 to 100, preferably approximately 90. Also called intrinsic viscosity, the K value is a parameter for characterizing polymers determined on the basis of relative viscosity by way of measuring the viscosities of polymer solutions.

Preferred vinylpyrrolidone homopolymers are available under the trade names Luviskol® K 30, Luviskol® K 80, Luviskol® K 85 and Luviskol® K 90, each from the BASF SE company. Most preferable in terms of the invention is Luviskol® K 90. Luviskol® K90 is a 20% aqueous solution of polyvinylpyrrolidone, colorless to pale yellow in color. The product has a K value of 90.0 to 98.0 (1% (m/V) in water), a solids content of 19.0 to 21.0% by weight and a pH of 7.0 to 9.0 (10% by weight solids content in water).

Combinations of at least one polyethylene glycol as component (a) and polyvinylpyrrolidone as film-forming agent (c) are commercially available, whereby the above-mentioned mixture is sold under the label of XO-Therm® (Chemsil Silicones Inc.). Preferred examples are specified as XO Therm® SP (INCI: PEG-4 (and) PEG-8 (and) PVP; viscosity RVT #2 @ 20 rpm: 1900 cs), XO Therm® CG (INCI: PEG-4 (and) PEG-8 (and) PVP; viscosity RVT #2 @ 20 rpm: 550 cs), XO Therm® IG (INCI: PEG-4 (and) PEG-8 (and) PVP; viscosity RVT #2 @ 20 rpm: 550 cs) and XO Therm® LH (INCI: propylene glycol (and) PEG-4 (and)

PEG-8 (and) PVP; viscosity RVT #2 @ 20 rpm: 150 cs). Particularly preferable in terms of the invention is XO Therm® IG.

If a mixture is used according to the invention composed of at least one polyethylene glycol (a) and polyvinylpyrrolidone as a film-forming agent (c), the cosmetic composition preferably includes the mixture in a quantity of from 20 to 80% by weight, preferably 50 to 75% by weight or 60 to 70% by weight based on the total weight of the cosmetic composition. Particularly preferable thereby is the use of a mixture of PEG-4 and PEG-8.

Based on the total weight of the mixture according to the invention, the inventive means includes a quantity of the vinylpyrrolidone homopolymer, for example, 1.0 to 12.0% by weight, preferably 2.0 to 10% by weight, further preferably 3.0 to 8.0% by weight, indicated respectively as the solids content of the active substance in the cosmetic composition.

Quaternary ammonium compounds are known components of styling agents, and examples of polyquaternium compounds may be polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-22, polyquaternium-24, polyquaternium-27, polyquaternium-28, polyquaternium-29, polyquaternium-30, polyquaternium-31, polyquaternium-32, polyquaternium-33, polyquaternium-34, polyquaternium-35, polyquaternium-36, polyquaternium-37, polyquaternium-39, polyquaternium-45, polyquaternium-46, polyquaternium-47, polyquaternium-48, polyquaternium-49, polyquaternium-50, polyquaternium-55 and polyquaternium-56. Particularly preferable in terms of the invention is polyquaternium-46. Polyquaternium-46 is commercially available, for example, under the name Luviquat® Hold AT2 as a 20% by weight aqueous solution. The use of Luviquat® Hold AT2 is preferable in terms of the invention.

If the cosmetic composition according to the invention includes a quaternary ammonium compound, it is in a preferable quantity of 0.1 to 2.0% by weight, further preferably 0.5 to 1.5% by weight based on the total weight of the cosmetic composition, whereby the quaternary ammonium compound thereby is preferably polyquaternium-46 (INCI).

The heating effect of the composition according to the invention can be further enhanced if the inventive composition further includes at least one hydrophobic or hydrophobized metal oxide powder, preferably a hydrophobic silicon dioxide, and further preferably hydrophobized pyrogenic silicon dioxide (fumed silica). The hydrophobization of the metal oxide can preferably be carried out using hexamethyldisilazane. One preferred example is specified as a hydrophobic fumed silica, which is obtained by treating hydrophilic silicon dioxide with hexamethyldisilazane, in particular hydrophilic fumed silicon dioxide having a specific surface area as measured by BET of approximately 200 to 400 m$^2$/g, more preferably approximately 300 m$^2$/g. This is commercially available under the name Aerosil® R812S (Evonik).

Another observed effect of the hydrophobic metal oxide powder usable according to the invention, in particular hydrophobicized silicon dioxide, is that of increased hair volume, so that the styling agent properties in regard to hair volume can be controlled by including a hydrophobic metal oxide powder.

The hydrophobic metal oxide powder according to the invention, in particular hydrophobicized silicon dioxide, is included in a quantity from 0.1 to 2.0% by weight, preferably from 0.5 to 1.5% by weight based on the total weight of the cosmetic composition.

The hair care effect of the composition according to the invention may be enhanced or modified by including additional lipophilic substances having a hair care effect. Oil bodies in particular are suitable as additional hair care substances. Counted as natural and synthetic cosmetic oil bodies are, for example, plant-based oils, liquid paraffin oils, isoparaffin oils and synthetic hydrocarbons as well as di-n-alkyl ethers comprising a total of 12 to 36 C atoms, in particular 12 to 24 C atoms. Plant-based oil bodies are preferable.

Substances particularly suited to hair care are dicarboxylic acid esters, symmetrical, asymmetrical or cyclic esters of carboxylic acid including fatty alcohols, tri-fatty acid esters of saturated and/or unsaturated linear and/or branched fatty acids including glycerin or partial glycerides of fatty acids, included among which are monoglycerides, diglycerides and technical mixtures thereof. An oil body preferable in terms of the invention is, for example, sweet almond oil.

The cosmetic means according to the invention may also include at least one oil body selected from the silicone oils group. The silicone oils group includes in particular the dimethicones, to which belong the cyclomethicones, the aminofunctional silicones as well as the dimethiconols. Dimethicones may be either linear or branched, cyclic, or cyclic and branched. Suitable silicone oils or silicone gums in particular are dialkyl and alkyl-aryl siloxane, for example dimethylpolysiloxane and methyl phenyl polysiloxane as well as alkoxylated, quaternized or anionic derivatives thereof. Preferable are cyclic and linear polydialkylsiloxanes, alkoxylated and/or aminated derivatives thereof, dihydroxypolydimethylsiloxanes and polyphenylalkylsiloxanes.

Ester oils, meaning esters of C6-C30 fatty acids having C2-C30 fatty alcohols, preferably monoesters of fatty acids with alcohols comprising 2 to 24 C atoms are further preferred hair care oil bodies, for example isopropyl myristate (Rilanit® IPM), isononanoic acid, C16-18-alkylesters (Cetiol® SN), 2-ethylhexyl palmitate (Cegesoft® 24), stearic acid, 2-ethylhexyl esters (Cetiol® 868), cetyl oleate, glycerin tricaprylate, coconut fatty alcohol caprate/caprylate (Cetiol® LC), n-butyl stearate, oleyl erucate (Cetiol® J 600), isopropyl palmitate (Rilanit® IPP), Oleyl oleate (Cetiol®), lauric acid, hexyl ester (Cetiol® A), di-n-butyl adipate (Cetiol® B), myristyl myristate (Cetiol® MM), cetearyl isononanoate (Cetiol® SN), oleic acid, decyl ester (Cetiol® V).

The means may also include at least one protein hydrolysate and/or a derivative thereof as a hair care substance. Protein hydrolysates are product mixtures obtained by breaking down proteins (albumins) by acid, base or enzyme catalysis. In terms of the invention, included under the term protein hydrolysates are also complete hydrolysates, individual amino acids and their derivates, as well as mixtures of various amino acids. The molecular weight of the protein hydrolysates usable according to the invention is between 75, the molecular weight for glycine, and 200,000, the molecular weight preferably being 75 to 50,000 and quite preferably 75 to 20,000 Daltons.

The composition according to the invention may include additional components commonly found in styling agents.

In embodiments of the invention, the present inventive cosmetic composition furthermore includes one or more component(s) that work as thickening or gelling agent(s), and are different from the film forming agents (c) described above, and which aid in film forming. Examples are cationic, anionic, nonionic or amphoteric polymers. The proportional weight of these additional components is, for example, 0.02 to 20% by weight, preferably 0.1 to 10.0% by weight of the cosmetic composition total, further preferably 1.0 to 5.0% by weight.

Examples include y acid (INCI: carbomer), different variations of which are commercially available under the name Carbopol®: acrylamide/ammonium acrylate copolymer, acrylamide/DMAPA acrylates/methoxy PEG methacrylate copolymer, acrylamidopropyltrimonium chloride/acrylamide copolymer, acrylamidopropyltrimonium chloride/acrylates copolymer, acrylates/acetoacetoxyethyl methacrylate copolymer, acrylates/acrylamide copolymer, acrylates/ammonium methacrylate copolymer, acrylates/t-butylacrylamide copolymer, acrylates copolymer, acrylates/C1-2 succinates/hydroxyacrylates copolymer, acrylates/lauryl acrylate/stearyl acrylate/ethyl amine oxide methacrylate copolymer, acrylates/octylacrylamide copolymer, acrylates/octylacrylamide/diphenyl amodimethicone copolymer, acrylates/stearyl acrylate/ethylamine oxide methacrylate copolymer, acrylates/VA copolymer, acrylates/VP copolymer, adipic acid/diethylenetriamine copolymer, adipic acid/dimethylaminohydroxypropyl diethylenetriamine copolymer, adipic acid/epoxypropyl diethylenetriamine copolymer, adipic acid/isophthalic acid/neopentyl glycol/trimethylolpropane copolymer, allyl stearate/VA copolymer, aminoethylacrylate phosphate/acrylates copolymer, aminoethylpropanediol-acrylates/acrylamide copolymer, aminoethylpropanediol-AMPD-acrylates/diacetoneacrylamide copolymer, ammonium VA/acrylates copolymer, AMPD-acrylates/diacetoneacrylamide copolymer, AMP-acrylates/allyl methacrylate copolymer, AMP-acrylates/C1-18 alkyl acrylates/C1-8 alkyl acrylamide copolymer, AMP-acrylates/diacetoneacrylamide copolymer, AMP-acrylates/dimethylaminoethylmethacrylate copolymer, bacillus/rice bran extract/soybean extract ferment filtrate, bis-butyloxyamodimethicone/PEG-60 copolymer, butyl acrylate/ethylhexyl methacrylate copolymer, butyl acrylate/hydroxypropyl dimethicone acrylate copolymer, butylated PVP, butyl ester of ethylene/MA copolymer, butyl ester of PVM/MA copolymer, calcium/sodium PVM/MA copolymer, corn starch/acrylamide/sodium acrylate copolymer, diethylene glycolamine/epichlorohydrin/piperazine copolymer, dimethicone crosspolymer, diphenyl amodimethicone, ethyl ester of PVM/MA copolymer, hydrolyzed wheat protein/PVP crosspolymer, isobutylene/ethylmaleimide/hydroxyethylmaleimide copolymer, isobutylene/MA copolymer, isobutylmethacrylate/bis-hydroxypropyl dimethicone acrylate copolymer, isopropyl ester of PVM/MA copolymer, lauryl acrylate crosspolymer, lauryl methacrylate/glycol dimethacrylate crosspolymer, MEA-sulfite, methacrylic acid/sodium acrylamidomethyl propane sulfonate copolymer, methacryloyl ethyl betaine/acrylates copolymer, octylacrylamide/acrylates/butylaminoethyl methacrylate copolymer, PEG/PPG-25/25 dimethicone/acrylates copolymer, PEG-8/SMDI copolymer, polyacrylamide, polyacrylate-6, poly-beta-alanine/glutaric Acid crosspolymer, polybutylene terephtalate, polyester-1, polyethyl acryl ate, polyethylene terephtalate, polymethacryloyl ethyl betaine, polypentaerythrityl terephthalate, polyperfluoroperhydrophenanthrene, polysilicone-9, polyurethane-1, polyurethane-6, polyurethane-10, polyvinyl acetate, polyvinyl butyral, polyvinylcaprolactam, polyvinylformamide, polyvinyl imidazolinium acetate, polyvinyl methyl ether, potassium butyl ester of PVM/MA copolymer, potassium ethyl ester of PVM/MA copolymer, PPG-70 polyglyceryl-10 ether, PPG-12/SMDI copolymer, PPG-51/SMDI copolymer, PPG-10 Sorbitol, PVM/MA copolymer, PVP, PVP/VA/itaconic acid copolymer, PVP/VA/vinyl propionate copolymer, rhizobian gum, rosin acrylate, shellac, sodium butyl ester of PVM/MA copolymer, sodium ethyl ester of PVM/MA copolymer, sodium polyacrylate, sterculia urens gum, terephthalic acid/isophthalic acid/sodium isophthalic acid sulfonate/glycol copolymer, trimethylolpropane triacrylate, trimethylsiloxysilylcarbamoyl pullulan, VA/crotonates copolymer, VA/crotonates/methacryloxybenzophenone-1 copolymer, VA/crotonates/vinyl neodecanoate copolymer, VA/crotonates/vinyl propionate copolymer, VA/DBM copolymer, VA/vinyl butyl benzoate/crotonates copolymer, vinylamine/vinyl alcohol copolymer, vinyl caprolactam/VP/dimethylaminoethyl methacrylate copolymer, VP/acrylates/lauryl methacrylate copolymer, VP/dimethylaminoethylmethacrylate copolymer, VP/DMAPA acrylates copolymer, VP/hexadecene copolymer, VP/VA copolymer, VP/vinyl caprolactam/DMAPA acrylates copolymer, yeast palmitate and styrene/VP copolymer.

Examples of nonionic polymers include:
Vinylpyrrolidone/vinyl ester copolymers, as marketed, for example, under the trademark Luviskol (BASF). Luviskol VA 64 and Luviskol VA 73, both vinyl pyrrolidone/vinyl acetate copolymers, are preferable nonionic polymers.

Ethers of cellulose, such as hydroxypropylcellulose, hydroxyethylcellulose and methylhydroxypropylcellulose, as marketed, for example, under the trademark Culminalund Benecel (AQUALON).

Shellac.

Siloxanes. These siloxanes may be water-soluble as well as non-water-soluble. Both volatile and non-volatile siloxanes are suitable, whereby non-volatile siloxanes refer to those connections having a boiling point exceeding 200° C. at standard pressure. Preferred siloxanes are polydialkylsiloxanes such as polydimethylsiloxane, polyalkylarylsiloxanes such as polyphenylmethylsiloxane, ethoxylated polydialkylsiloxanes, and polydialkylsiloxanes which include amino or hydroxyl groups.

Glycosidic silicone substitute.

The means according to the invention may also include a cosmetically acceptable preserving agent. An example of a preferred preservative suitable for use is 2-phenoxyethanol.

The means according to the invention may also include a cosmetically acceptable fragrance or perfume.

The cosmetic composition for the temporary shaping of hair may be manufactured in the forms typical for temporarily shaping hair, such as styling cream or styling paste, hair gel, wax, cream, paste, foam or lotion. The cosmetic composition according to the invention exists in particular as a viscous liquid, whereby this manufactured state can also be described as a styling serum.

The present invention also relates to the use of a cosmetic composition according to the invention for temporarily shaping keratin fibers, in particular human hair, as well as a method for temporarily shaping keratin fibers, in particular human hair, in which the cosmetic composition according to the invention is applied to keratin fibers.

Summary Table

The composition of several preferred cosmetic means may be gathered from the following tables (unless otherwise specified, indicated as solids content and in % by weight based on the total weight of the cosmetic means).

|  | Formula 1 | Formula 2 | Formula 3 | Formula 4 |
|---|---|---|---|---|
| Polyethylene glycol having 4 to 20 oxyethylene units (a) | 15.0 to 80.0 | 25.0 to 80.0 | 45.0 to 75.0 | 55.0 to 70.0 |
| Copolymer of hydrogenated castor oil and an n-alkyl dicarboxylic acid having 4 to 10 C atoms (b) | 0.05 to 3.0 | 0.1 to 2.5 | 0.2 to 2.0 | 0.5 to 1.5 |
| Film forming agent (c) | 0.01 to 5.0 | 0.02 to 3.0 | 0.1 to 2.5 | 0.2 to 2.0 |
| Glycerin, purity ≥99.5% | 10 to 80 | 20 to 60 | 20 to 40 | 25 to 35 |
| Misc. | add 100 | add 100 | add 100 | add 100 |

|  | Formula 1a | Formula 2a | Formula 3a | Formula 4a |
|---|---|---|---|---|
| Component (a): PEG-4 and PEG-8 | 15.0 to 80.0 | 25.0 to 80.0 | 45.0 to 75.0 | 55.0 to 70.0 |
| Component (b): Oligoester of hydrogenated castor oil and sebacic acid, in particular Crodabond ® CSA* | 0.05 to 3.0 | 0.1 to 2.5 | 0.2 to 2.0 | 0.5 to 1.5 |
| Film forming agent (c): polyvinylpyrrolidone | 0.01 to 5.0 | 0.02 to 3.0 | 0.1 to 2.5 | 0.2 to 2.0 |
| Glycerin, purity ≥99.5% | 10 to 80 | 20 to 60 | 20 to 40 | 25 to 35 |
| Misc. | add 100 | add 100 | add 100 | add 100 |

|  | Formula 1b | Formula 2b | Formula 3b | Formula 4b |
|---|---|---|---|---|
| Mixture of PEG-4, PEG-8 and polyvinylpyrrolidone, in particular XO-Therm ® IG | 20.0 to 85.0 | 30.0 to 85.0 | 50.0 to 80.0 | 60.0 to 75.0 |
| Component (b): Oligoester of hydrogenated castor oil and sebacic acid, in particular Crodabond ® CSA* | 0.05 to 3.0 | 0.1 to 2.5 | 0.2 to 2.0 | 0.5 to 1.5 |
| Glycerin, purity ≥99.5% | 10 to 80 | 20 to 60 | 20 to 40 | 25 to 35 |
| Misc. | add 100 | add 100 | add 100 | add 100 |

|  | Formula 11 | Formula 12 | Formula 13 | Formula 14 |
|---|---|---|---|---|
| Polyethylene glycol having 4 to 20 oxyethylene units (a) | 15.0 to 80.0 | 25.0 to 80.0 | 45.0 to 75.0 | 55.0 to 70.0 |
| Copolymer of hydrogenated castor oil and an n-alkyl dicarboxylic acid having 4 to 10 C atoms (b) | 0.05 to 3.0 | 0.1 to 2.5 | 0.2 to 2.0 | 0.5 to 1.5 |
| Film forming agent (c) | 0.01 to 5.0 | 0.02 to 3.0 | 0.1 to 2.5 | 0.2 to 2.0 |
| Quaternary ammonium compound | 0.01 to 0.5 | 0.02 to 0.4 | 0.05 to 0.35 | 0.1 to 0.3 |
| Glycerin, purity ≥99.5% | 10 to 80 | 20 to 60 | 20 to 40 | 25 to 35 |
| Misc. | add 100 | add 100 | add 100 | add 100 |

|  | Formula 11a | Formula 12a | Formula 13a | Formula 14a |
|---|---|---|---|---|
| Component (a): PEG-4 and PEG-8 | 15.0 to 80.0 | 25.0 to 80.0 | 45.0 to 75.0 | 55.0 to 70.0 |
| Component (b): Oligoester of hydrogenated castor oil and sebacic acid, in particular Crodabond ® CSA* | 0.05 to 3.0 | 0.1 to 2.5 | 0.2 to 2.0 | 0.5 to 1.5 |
| Film forming agent (c): polyvinylpyrrolidone | 0.01 to 5.0 | 0.02 to 3.0 | 0.1 to 2.5 | 0.2 to 2.0 |
| Polyquaternium-46 | 0.01 to 0.5 | 0.02 to 0.4 | 0.05 to 0.35 | 0.1 to 0.3 |
| Glycerin, purity ≥99.5% | 10 to 80 | 20 to 60 | 20 to 40 | 25 to 35 |
| Misc. | add 100 | add 100 | add 100 | add 100 |

|  | Formula 11b | Formula 12b | Formula 13b | Formula 14b |
|---|---|---|---|---|
| Mixture of PEG-4, PEG-8 and polyvinylpyrrolidone, in particular XO-Therm ® IG | 20.0 to 85.0 | 30.0 to 85.0 | 50.0 to 80.0 | 60.0 to 75.0 |
| Component (b): Oligoester of hydrogenated castor oil and sebacic acid, in particular Crodabond ® CSA* | 0.05 to 3.0 | 0.1 to 2.5 | 0.2 to 2.0 | 0.5 to 1.5 |
| Polyquaternium-46 | 0.01 to 0.5 | 0.02 to 0.4 | 0.05 to 0.35 | 0.1 to 0.3 |
| Glycerin, purity ≥99.5% | 10 to 80 | 20 to 60 | 20 to 40 | 25 to 35 |
| Misc. | add 100 | add 100 | add 100 | add 100 |

|  | Formula 21 | Formula 22 | Formula 23 | Formula 24 |
|---|---|---|---|---|
| Polyethylene glycol having 4 to 20 oxyethylene units (a) | 15.0 to 80.0 | 25.0 to 80.0 | 45.0 to 75.0 | 55.0 to 70.0 |
| Copolymer of hydrogenated castor oil and an n-alkyl dicarboxylic acid having 4 to 10 C atoms (b) | 0.05 to 3.0 | 0.1 to 2.5 | 0.2 to 2.0 | 0.5 to 1.5 |

-continued

| | | | | |
|---|---|---|---|---|
| Film forming agent (c) | 0.01 to 5.0 | 0.02 to 3.0 | 0.1 to 2.5 | 0.2 to 2.0 |
| Hydrophobic metal oxide powder | 0.05 to 5.0 | 0.1 to 3.0 | 0.2 to 2.0 | 0.5 to 1.5 |
| Glycerin, purity ≥99.5% | 10 to 80 | 20 to 60 | 20 to 40 | 25 to 35 |
| Misc. | add 100 | add 100 | add 100 | add 100 |

| | Formula 21a | Formula 22a | Formula 23a | Formula 24a |
|---|---|---|---|---|
| Component (a): PEG-4 and PEG-8 | 15.0 to 80.0 | 25.0 to 80.0 | 45.0 to 75.0 | 55.0 to 70.0 |
| Component (b): Oligoester of hydrogenated castor oil and sebacic acid, in particular Crodabond ® CSA* | 0.05 to 3.0 | 0.1 to 2.5 | 0.2 to 2.0 | 0.5 to 1.5 |
| Film forming agent (c): polyvinylpyrrolidone | 0.01 to 5.0 | 0.02 to 3.0 | 0.1 to 2.5 | 0.2 to 2.0 |
| Hydrophobic silicon dioxide, in particular Aerosil ® R812 S | 0.05 to 5.0 | 0.1 to 3.0 | 0.2 to 2.0 | 0.5 to 1.5 |
| Glycerin, purity ≥99.5% | 10 to 80 | 20 to 60 | 20 to 40 | 25 to 35 |
| Misc. | add 100 | add 100 | add 100 | add 100 |

| | Formula 21b | Formula 22b | Formula 23b | Formula 24b |
|---|---|---|---|---|
| Mixture of PEG-4, PEG-8 and polyvinylpyrrolidone, in particular XO-Therm ® IG | 20.0 to 85.0 | 30.0 to 85.0 | 50.0 to 80.0 | 60.0 to 75.0 |
| Component (b): Oligoester of hydrogenated castor oil and sebacic acid, in particular Crodabond ® CSA* | 0.05 to 3.0 | 0.1 to 2.5 | 0.2 to 2.0 | 0.5 to 1.5 |
| Hydrophobic silicon dioxide, in particular Aerosil ® R812 S | 0.05 to 5.0 | 0.1 to 3.0 | 0.2 to 2.0 | 0.5 to 1.5 |
| Glycerin, purity ≥99.5% | 10 to 80 | 20 to 60 | 20 to 40 | 25 to 35 |
| Misc. | add 100 | add 100 | add 100 | add 100 |

| | Formula 31 | Formula 32 | Formula 33 | Formula 34 |
|---|---|---|---|---|
| Polyethylene glycol having 4 to 20 oxyethylene units (a) | 15.0 to 80.0 | 25.0 to 80.0 | 45.0 to 75.0 | 55.0 to 70.0 |
| Copolymer of hydrogenated castor oil and an n-alkyl dicarboxylic acid having 4 to 10 C atoms (b) | 0.05 to 3.0 | 0.1 to 2.5 | 0.2 to 2.0 | 0.5 to 1.5 |
| Film forming agent (c) | 0.01 to 5.0 | 0.02 to 3.0 | 0.1 to 2.5 | 0.2 to 2.0 |
| Quaternary ammonium compound | 0.01 to 0.5 | 0.02 to 0.4 | 0.05 to 0.35 | 0.1 to 0.3 |
| Hydrophobic metal oxide powder | 0.05 to 5.0 | 0.1 to 3.0 | 0.2 to 2.0 | 0.5 to 1.5 |
| Glycerin, purity ≥99.5% | 10 to 80 | 20 to 60 | 20 to 40 | 25 to 35 |
| Misc. | add 100 | add 100 | add 100 | add 100 |

| | Formula 31a | Formula 32a | Formula 33a | Formula 34a |
|---|---|---|---|---|
| Component (a): PEG-4 and PEG-8 | 15.0 to 80.0 | 25.0 to 80.0 | 45.0 to 75.0 | 55.0 to 70.0 |
| Component (b): Oligoester of hydrogenated castor oil and sebacic acid, in particular Crodabond ® CSA* | 0.05 to 3.0 | 0.1 to 2.5 | 0.2 to 2.0 | 0.5 to 1.5 |
| Film forming agent (c): polyvinylpyrrolidone | 0.01 to 5.0 | 0.02 to 3.0 | 0.1 to 2.5 | 0.2 to 2.0 |
| Polyquaternium-46 | 0.01 to 0.5 | 0.02 to 0.4 | 0.05 to 0.35 | 0.1 to 0.3 |
| Hydrophobic silicon dioxide, in particular Aerosil ® R812 S | 0.05 to 5.0 | 0.1 to 3.0 | 0.2 to 2.0 | 0.5 to 1.5 |
| Glycerin, purity ≥99.5% | 10 to 80 | 20 to 60 | 20 to 40 | 25 to 35 |
| Misc. | add 100 | add 100 | add 100 | add 100 |

| | Formula 31b | Formula 32b | Formula 33b | Formula 34b |
|---|---|---|---|---|
| Mixture of PEG-4, PEG-8 and polyvinylpyrrolidone, in particular XO-Therm ® IG | 20.0 to 85.0 | 30.0 to 85.0 | 50.0 to 80.0 | 60.0 to 75.0 |
| Component (b): Oligoester of hydrogenated castor oil and sebacic acid, in particular Crodabond ® CSA* | 0.05 to 3.0 | 0.1 to 2.5 | 0.2 to 2.0 | 0.5 to 1.5 |
| Polyquaternium-46 | 0.01 to 0.5 | 0.02 to 0.4 | 0.05 to 0.35 | 0.1 to 0.3 |

-continued

| | | | | |
|---|---|---|---|---|
| Hydrophobic silicon dioxide, in particular Aerosil ® R812 S | 0.05 to 5.0 | 0.1 to 3.0 | 0.2 to 2.0 | 0.5 to 1.5 |
| Glycerin, purity ≥99.5% | 10 to 80 | 20 to 60 | 20 to 40 | 25 to 35 |
| Misc. | add 100 | add 100 | add 100 | add 100 |

*indicated as solids content

In terms of the invention, "Misc." refers to additional components commonly found in styling products. These include in particular plant-based oils such as sweet almond oil, which may, for example, be included in the cosmetic composition at approximately 0.2 to 1.0% by weight, preferably approximately 0.5% by weight.

Examples

The following styling agents were produced:

| Component/ Raw material | INCI or other name | Manufacturer | 1 (% by weight) | 2 (% by weight) | 3 (% by weight) |
|---|---|---|---|---|---|
| XO Therm ® IG | PEG-4 (and) PEG-8 (and) PVP | Chemsil Silicones | 70.0 | 70.0 | 70.0 |
| Glycerin 99.5% | | | 27.3 | 27.3 | 27.3 |
| Luviquat ® Hold AT2 | Polyquaternium-46 | BASF | 1.0 | — | 0.5 |
| Almond oil, sweet | | | 0.5 | 0.5 | 0.5 |
| Crodabond ® CSA-LQ-(JP) | Hydrogenated Castor Oil/Sebacic Acid Copolymer | Croda | 1.0 | 1.0 | 1.0 |
| Perf Golden Flower 891432 | | | 0.20 | 0.20 | 0.20 |
| Aerosil R812S | Hydrophobic fumed silica | Evonik | — | 1.0 | 0.50 |
| Total | | | 100 | 100 | 100 |

The quantities in the table are indicated in % by weight of the respective raw material based on the entire composition.

Styling agent 1: styling agent with heating and hair care effects.

Damaged hair was treated with styling agent 1 by carefully distributing a predetermined amount in towel-dried yet still damp hair. Prior to the treatment with styling agent 1, there were microscopically visible split ends and the cuticle layer was damaged. Following the treatment, microscopic analysis showed significant reduction in the split ends and the cuticle layer damage.

Styling agent properties such as imparting a good, lasting hairstyle hold without frizzing the hair were also achieved.

It was observed that heat was generated by rubbing between the hands as well as by distribution in the hair.

Styling agent 2: stronger styling agent with heating, hair care and volume effects.

Results similar to those for styling agent 1 were observed with respect to the repair of damaged hair.

The heat generation effect was significantly enhanced in styling agent 2. A good, lasting hairstyle hold was able to be obtained along with increased hair volume.

Styling agent 3: stronger styling agent with heating, hair care and volume effects as well as stronger hold.

Results similar to those for styling agent 2 were observed with respect to the repair of damaged hair and the generation of heat.

The styling hold was stronger than in styling agents 1 and 2.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. Cosmetic composition having a heating effect and used for the care and temporary shaping of keratin fibers, comprising:
    (a) at least one polyethylene glycol comprising 4 to 20 oxyethylene units;
    (b) a copolymer composed of hydrogenated castor oil and an n-alkyl dicarboxylic acid comprising 4 to 10 C atoms;
    (c) at least one film-forming agent; and
    (d) a hydrophobic silicon dioxide powder obtained by treating silicon dioxide with hexamethyldisilazane.

2. The cosmetic composition according to claim 1, wherein one or more polyethylene glycols comprising 4 to 10 oxyethylene units is included as component (a).

3. The cosmetic composition according to claim 1, wherein a mixture of PEG-4 and PEG-8 is included as component (a).

4. The cosmetic composition according to claim 1, wherein component (b) is an oligoester of hydrogenated castor oil and sebacic acid.

5. The cosmetic composition according to claim 1, wherein a polymer selected from the group consisting of: polyvinylpyrrolidone, quaternary ammonium cations, and combinations thereof is included as a film-forming agent (c).

6. The cosmetic composition according to claim 5, wherein a polyvinylpyrrolidone or a combination of a polyvinylpyrrolidone and polyquaternium-46 (INCI) is included as the film-forming agent (c).

7. The cosmetic composition according to claim 1, wherein the composition includes less than 1.0% by weight free water based on the total weight of the composition.

8. The cosmetic composition according to claim 1, wherein the composition includes less than 0.5% by weight free water based on the total weight of the composition.

9. The cosmetic composition according to claim 1, wherein the composition includes 20% by weight or more of glycerine based on the total weight of the cosmetic composition.

10. The cosmetic composition according to claim 1, wherein, based on the total weight of the cosmetic composition, the composition includes 0.1 to 2.0% by weight of the copolymer (b) composed of hydrogenated castor oil and an n-alkyl dicarboxylic acid comprising 4 to 10 carbon atoms.

* * * * *